United States Patent [19]

Wyatt et al.

[11] Patent Number: 4,621,063
[45] Date of Patent: Nov. 4, 1986

[54] METHODS FOR THE DETECTION AND QUANTITATION OF IMMUNOLOGICAL SUBSTANCES

[75] Inventors: Philip J. Wyatt, Santa Barbara; Alberto F. Lopapa, Los Angeles, both of Calif.

[73] Assignee: The Center for Immunological Studies, Los Angeles, Calif.

[21] Appl. No.: 433,732

[22] Filed: Oct. 12, 1982

[51] Int. Cl.$^4$ ............................................ G01N 33/543
[52] U.S. Cl. .................................... 436/501; 436/513; 436/518; 436/805; 436/807; 422/67; 422/73; 356/38; 356/371
[58] Field of Search ............... 436/501, 513, 514, 518, 436/807, 816, 817, 815, 63, 164, 169, 165, 909, 805; 422/67, 73; 356/38, 371

[56] References Cited

U.S. PATENT DOCUMENTS

| | | | |
|---|---|---|---|
| 3,720,760 | 3/1973 | Bennich et al. | 436/513 |
| 3,804,521 | 4/1974 | Sprague | 356/371 |
| 3,905,767 | 9/1975 | Morris et al. | 436/513 |
| 4,011,044 | 3/1977 | Uzgiris | 436/805 |

Primary Examiner—Esther M. Kepplinger
Attorney, Agent, or Firm—Frank Frisenda, Jr.

[57] ABSTRACT

The invention provides improved methods and unique instrumentation for the detection and for the quantitation of chemical substances and has particular application for the detection and for the quantitation of immunological substances. In one embodied form, the inventive method comprises the steps of (a) affixing to a surface a reactant material known to interact and to bind to, or to have a relatively high affinity for, the immunological substance to be detected, the substance being present in at least one medium; (b) impinging the affixed surface with a source of coherent radiation; (c) measuring a pattern of radiation scattered from the affixed surface; (d) reacting the affixed surface with at least one medium containing the immunological substance; (e) impinging the reacted affixed surface with substantially the same coherent radiation at substantially the same aspect and orientation utilized to perform step (b); (f) measuring a pattern of radiation scattered from the reacted affixed surface; and (g) comparing the patterns of radiation derived from steps (b) and (f) to determine any differentiations therebetween. The unique instrumentation provides a complete system for convenient, precise quantitative measurement of immunological substances sought to be detected. The inventive methods and instrumentation thereby provide an extremely sensitive, yet relatively rapid, means for quantitative and qualitative analyses which has application to a broad range of biological fields.

30 Claims, 5 Drawing Figures

METHODS FOR THE DETECTION AND QUANTITATION OF IMMUNOLOGICAL SUBSTANCES

BACKGROUND OF THE INVENTION

The detection and quantitation of chemical substances including immunological substances represents an ongoing problem for many diverse disciplines. In the environmental area, for instance, the detection of dangerous compounds in air, water, and earth often requires extensive chemical tests and analyses. Certain carcinogens are excluded by fiat at any level in drinking waters, yet their detection even at relatively high levels is often impossible because of a lack of sensitivity of conventional testing. As more substances are recognized to be dangerous to the health of humans, new tests and analytical techniques will be required.

In the context of the present invention, the detection and quantitation of relatively small amounts of specific immunological substances such as immunoglobulin IgE is especially important for the diagnosis and for the treatment of allergenic reaction of certain individuals. Generally, such substances are present at extremely low levels in human serum. Accordingly, the detection and quantitation of certain types of IgE and their association with particular allergens can be well correlated with specific allergies experienced by the serum donor.

A further area wherein the detection and quantitation of a particular chemical substance is desirable, if not mandatory, is the field of virology. Viruses are generally believed to be complex molecules of DNA surrounded by a protein sheath and, as such, are said to represent the very smallest of life forms. They are thought to be the causitive agents of many diseases such as hepatitis, herpes, mumps, polyomyolitis, among others, and have already been identified with various types of cancer. The importance of detecting such viruses, at an early stage, of course, cannot be overstated.

Thus, the detection of the aforementioned chemical substances and other similar substances has represented a critical but most difficult, and, in some cases impossible task.

Extensive analytical, spectroscopic, radioisotopic, and biological test procedures have been developed in an attempt to fulfill these detection requirements. However, many conventional procedures are relatively insensitive yet rapid, while other procedures are extremely sensitive, yet relatively slow.

Typically, the specific chemical substances sought to be detected have been determined by one or two best specialized techniques or procedures. Despite the plethera of methods, no one methodology represents an ideal solution for the multitude of specific substances and no one method lends itself to universal application. Radioimmunoassay techniques, however, do have very broad ranges of applicability for chemical substances of biological origin.

New approaches for such detection and quantitation are constantly sought and with each, a commensurate new range of detection possibilities thereby results.

Among these approaches are the multitude of specific assays utilizing optical analyzers, for instance, those disclosed in the following U.S. Patents issued to Philip J. Wyatt as sole or joint inventor: U.S. Pat. No. 3,624,835—*Microparticle Analyzer Employing a Spherical Detector Array*, (Nov. 30, 1971); U.S. Pat. No. 3,730,842—*Process for Determining Bacterial Drug Sensitivity* with R. M. Berkman and D. T. Phillips (May 1, 1973); U.S. Pat. No. 3,754,830—*Scattering Cell Employing Electrostatic Means for Supporting a Particle* with D. T. Phillips, H. H. Brooks and C. R. Liu (Aug. 28, 1973); U.S. Pat. No. 3,770,351—*Optical Analyzer for Microparticles* (Nov. 6, 1973); U.S. Pat. No. 3,815,000—*Levitator* with D. T. Phillips, H. H. Brooks and C. R. Liu (June 4, 1974); U.S. Pat. No. 3,928,140—*Apparatus and Process for Testing Microparticle Response to its Environment* with V. R. Stull, W. L. Proctor and I. L. Miller (Dec. 25, 1975); and U.S. Pat. No. 4,101,383—*Apparatus and Process for Testing Microparticle Response to its Environment*—with V. R. Stull, W. L. Proctor and I. L. Miller (July 18, 1978).

Such disclosures are hereby specifically incorporated by this reference.

Accordingly, those skilled in the art have recognized a significant need for a sensitive yet relatively rapid detection and quantitation technique which lends itself to a broad range of applications. The present invention fulfills these needs.

SUMMARY OF THE INVENTION

This invention relates to improved methods and unique instrumentation for the detection and for the quantitation of chemical substances and has particular application for the detection and for the quantitation of immunological substances.

In one embodied form, the inventive method comprises the steps of (a) affixing to a surface a reactant material known to interact and to bind to, or to have a relatively high affinity for, the immunological substance to be detected, the substance being present in at least one medium; (b) impinging the affixed surface with a source of coherent radiation; (c) measuring a pattern of radiation scattered from the affixed surface; (d) reacting the affixed surface with at least one medium containing the immunological substance; (e) impinging the reacted affixed surface with substantially the same coherent radiation at substantially the same aspect and orientation utilized to perform step (b); (f) measuring a pattern of radiation scattered from the reacted affixed surface; and (g) comparing the patterns of radiation derived from steps (b) and (f) to determine any differentiations therebetween.

The scattering of coherent light from a surface therefore results in the formation of speckled patterns which may be observed by any conventional means, such as the naked eye or projected on to a screen. The degree of speckle is preferably quantitatively measured by suitable measurement means such as a photometric detector or the like. Moreover, detection means by which the relative change of speckle pattern may be observed and regular low frequency features detected on a background of relatively higher frequency speckle, such as by spatial filtering, may be utilized to compare the foregoing measured patterns and thereby determine any differentiations therebetween.

In a presently preferred embodiment, the inventive method and instrumentation is utilized in conjunction with a solid support surface such as a transparent vial or test tube comprising a diffuser at a base portion thereof. When suitably positioned with respect to the source of coherent radiation, a variety of complex internal reflections permit the exposure of the affixed surface to the coherent radiation and a portion of such radiation is transmitted through and out of an open portion of the tube. The escaping radiation from the tube is directed towards a lens and aperture means depending upon the degree of frequency filtering desired.

Accordingly, the foregoing embodiment permits spatial filtering of high or low frequency features of the speckle pattern whose visibility may be augmented by pattern recognition procedures, rotating grids and masks, as well as other known type of signal processing and enhancement techniques.

In particular, if the pattern image is projected on a multipixel detection device then each resolution cell of the image, corresponding to the size of the pixel, will yield a digital value for storage in for instance, a computer memory means characteristic of the photon flux incident upon the pixel during the time of measurement.

In yet another embodiment of the invention, means for periodic rotation of the affixed surface is provided to preferably rotate the surface co-axially with the incident coherent radiation source producing a rotation of the scatter pattern. With rotation of the surface and corresponding rotation of the scatter pattern, the pattern may be analyzed by appropriate analysis methods and averaged over time and/or orientation to enhance precision of the final analytical determination.

The unique instrumentation therefore provides a complete system for convenient, precise, quantitative measurement of immunological substances sought to be detected. The inventive methods and instrumentation accordingly provide an extremely sensitive, yet relatively rapid, means for quantitative and qualitative analysis which has application to a broad range of biological fields.

The above and other objects and advantages will become apparent from the following more detailed description of the invention, taken in conjunction with the drawings.

DESCRIPTION OF THE PREFERRED EMBODIMENTS

Figure 1:
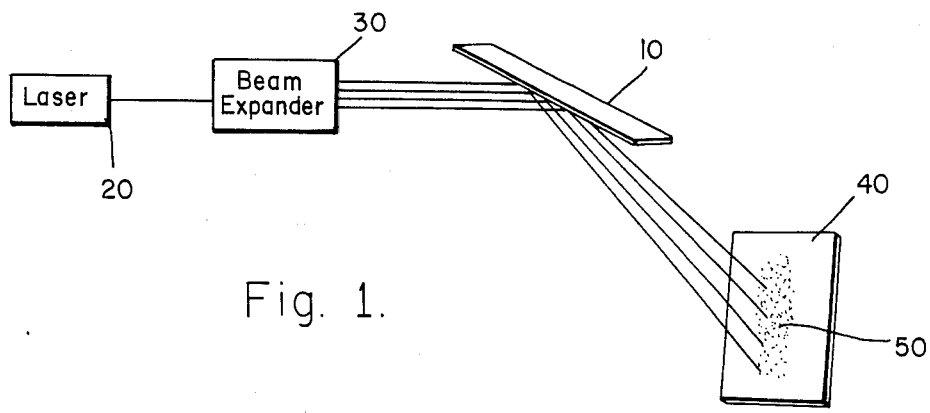
FIG. 1 is a schematic drawing of one illustrative embodiment for performing a method for the detection and quantitation of a chemical substance in accordance with the present invention.

The present invention describes a unique approach for detection procedures and various instrumentation implementation thereof based on the use of coherent radiation.

Long before the development of the laser, the measurement and theory of coherent radiation had been developed by von Laue, van Cittert, Berek, Zernike, Wolf, among others. One technique, utilized the interference between two light sources, $P_1$ and $P_2$ at some distant point Q. The degree of interference at Q is related to the degree of coherence of the sources $P_1$ and $P_2$.

With the advent of the laser and its extremely great coherence properties, a variety of multiple source coherent effects were immediately noted and foremost among such effects was the phenomenon of speckle.

The speckle phenomenon is usually observed when a laser beam is reflected off of a surface. Since the incident laser wave front is coherent, each reflected contribution is highly coherent with respect to all others. Upon observing the reflected light, one observes a speckled appearance of the illuminated surface. This is believed to occur due to the interferences between wavelets originating from different parts of the surface.

Were the surface absolutely smooth, one would not observe speckle which is commensurate with the inherent roughness of the surface observed. As the angle between the direction of the incident source and the direction of observation becomes larger, the degree of speckle generally increases.

Accordingly, for a source of coherent radiation such as a laser, it is very difficult to eliminate these effects even after passing the laser beam through various diffusers before incidence on the surface. The laser light is said, therefore, to have a very large coherence length.

The scattering of the coherent light from a surface therefore results in the formation of speckled patterns which may be observed by the naked eye or projected on to a screen. The degree of speckle or mottled appearance is proportional to the inherent roughness of the surface examined, as well as the angle of incident of the light, the angle of observation of the scattered or transmitted light and the wave length and polarization of the incident light.

Accordingly, any change in the surface properties that affect its roughness or regularity, will produce an associated change in the speckle pattern produced, though these changes may be relatively slight. Thus, the adherence to or erosion from a surface, for instance, resulting from chemical reaction will affect the resultant pattern produced by the reacted surface.

The present invention provides unique methods and instrumentation for the detection and for the quantitation of immunological substances, for instance, present in a gaseous, fluid or solid medium, or combination thereof.

In one embodied form, the inventive method comprises the steps of: (a) affixing to a surface a reactant material known to interact with, to bind to, or to have a relatively high affinity for, the immunological substance to be detected, the substance being present in at least one medium; (b) impinging the affixed surface with a source of coherent radiation; (c) measuring a pattern of radiation scattered from the affixed surface; (d) reacting the affixed surface with at least one medium containing the immunological substance; (e) impinging the reacted affixed surface with substantially the same coherent radiation at substantially the same aspect and orientation utilized to perform step (b); (f) measuring a pattern of radiation scattered from the reacted affixed surface; and (g) comparing the patterns of radiation derived from steps (b) and (f) to determine any differentiations therebetween. The inventive methods and unique instrumentation thereby provide an extremely sensitive, yet relatively rapid, means for quantitative and qualitative analyses which is applicable to a broad range of biological fields.

With reference to the description of the invention herein, the following definitions will be helpful to an understanding of the spirit and scope of the invention as applied to detection and quantitation of immunological substances.

The term "immunological substance" refers generally to any form of native or complex protein or a mixture of compounds having specific affinities for other chemical groups or compounds solely generated by the triggering effect of the immune system. Such substances include, but are not limited to, native and/or complex proteins found on cell surfaces, for instance, antibodies, antigens, allergens and the like.

The term "antibody" refers generally to a resultant protein produced in the immune system of an animal in response to stimulation by the introduction of a foreign protein.

The term "antigen" refers generally to a substance or part of a substance that stimulates an immune response and subsequent production of antibodies specific thereto.

The term "allergen" refers generally to a substance producing an antibody response in man or other animal life including mono and poly clonal antibodies.

The term "radiation" refers generally to electromagnetic radiation such as light, x-rays, infra red and/or other electromagnetic waves.

The term "scattering" refers generally to the phenomena connected with the changing of an incident radiation associated with but not limited to its change of direction, frequency, intensity and/or polarization.

The term "surface" refers generally to any interface separating two media and/or phases.

Referring now to the drawings, denoted FIG. 1, there is depicted in schematic form one illustrative embodiment for performing a method for the detection and quantitation of an immunological substance, for instance antibodies present in a liquid medium such as human serum.

A surface 10, such as microscope slide or the like, has affixed thereto an immunological substance, for instance, an antigen. The affixation may be accomplished by any known means such as by thermal treatment or chemical treatment, among others.

The prepared surface 10 (hereinafter referred to as "the affixed suface") now carrying a reactant material known to interact and to bind to an immunological substance to be detected is initially impinged with means for supplying coherent radiation such as laser source 20. Optionally mounted in association with the laser 20 is means 30, such as a beam expander, which enlarges the area of the affixed surface 10 impinged by the coherent radiation thereby commensurately increasing the area of the affixed surface 10 qualitatively and quantitatively examined.

Those skilled in the art will readily appreciate that the use of means for modifying the coherent radiation prior to impingement is optional and clearly not mandatory in accordance with the present invention. For instance, where a relatively small selected portion of the affixed surface 10 is to be analyzed, no expansion of the laser beam is required. Moreover, the coherent radiation may be modified by any desired means such as with a beam diffuser, a beam filter or other known modifying means.

Upon impingement on the affixed surface 10, a portion of the radiation is scattered and directed to detection means 40 such as screen, producing a speckle pattern 50 displayed thereon.

Owing to the relatively high degree of coherency still remaining in the scattered radiation, the relative roughness of the surface of screen 40 itself may contribute to the speckle observed. However, in general, this contribution will be a small constant fraction of the total speckle pattern produced thereon, and will not interfere with accuracy and precision of the instant methodology.

Those skilled in the art will readily appreciate that a wide variety of detection means 40 may alternatively be utilized to observe the speckle pattern 50 corresponding to the character of the affixed surface 10. For instance, by placing the eye at the screen position and looking toward the illuminated affixed surface 10, the speckle 50 is readily observed.

The speckle pattern 50, accordingly is preferably quantitatively measured by suitable measurement means such as a photometric detector or the like.

Thereafter, the affixed surface 10, for instance, carrying the antigen is reacted with the fluid medium or media to be tested. After sufficient time for reaction, varying from a few seconds to twenty-four hours as called for by the specific assay, the excess fluid is discarded.

Following the contact between the affixed surface 10 and the medium or media to be tested, the now "reacted affixed surface" may optionally be treated, for instance, incubated, washed, dried or further conventionally treated, as called for by the specific substance sought to be detected. It should be understood, however, that such subsequent treatment may not be required depending upon the substances used and the sensitivity of the assay to be performed in accordance with the present invention.

The reacted affixed surface is again impinged with substantially the same coherent radiation at substantially the same aspect and orientation utilized for previously measuring the affixed surface 10.

Thereafter, another measurement of the speckle pattern 50' of radiation scattered from the reacted affixed surface is made and optionally quantified. The speckle pattern 50' is then compared with the speckle pattern 50 previously measured.

With reference to detection of immunological substances, the attachment or the affinity of antibodies to antigenic sights affixed to a surface was observed to result in a microscopic regular roughness on a relatively smooth support surface.

Accordingly, after passage of highly coherent light directed therefrom or therethrough, a resultant speckle pattern has been produced having a relatively high degree of striated organization in addition to remnants of the surviving speckle pattern. It is believed that the degree of organized striation may be correlated as a direct measure of the amount of antibodies which have combined with surface affixed antigen.

Those skilled in the art will readily appreciate that there are many means by which the relative change of speckle pattern may be observed and regular low frequency features detected on a background of relatively higher frequency speckle. One example of such means is spatial filtering described herein in more detail.

Figure 2:
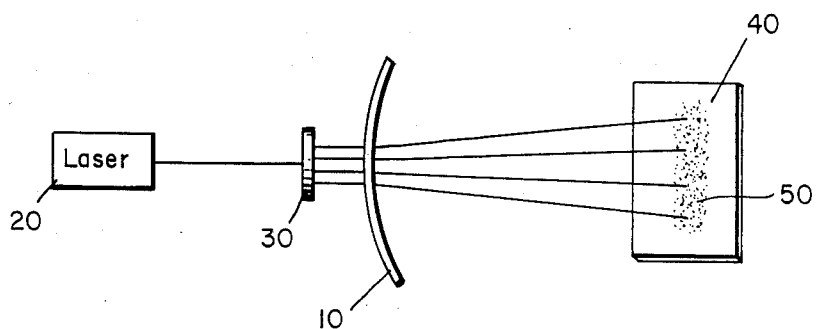
FIG. 2 is a schematic drawing of a second illustrative embodiment for performing a method for the detection and quantitation of a chemical substance utilizing an affixed surface possessing prescribed transmission characteristics.

Referring now to FIG. 2, there is illustrated a second embodied method in accordance with the present invention wherein a reactant material known to interact and to bind to or to have a relatively high affinity for a substance to be detected is affixed to surface 10. The surface 10 in this embodied form is of the type having prescribed transmission characteristics and may preferably be transparent.

As in the prior embodiment herein, the affixed surface 10 is impinged with coherent radiation such as derived from laser source 20. The laser beam optionally is modified by a beam diffuser 30, for instance, a lens of relatively short focal length commensurate with the area to be impinged.

The resultant pattern of coherent radiation transmitted through the affixed surface is appropriately measured as previously described. Thereafter, the affixed surface is reacted with at least one medium to be tested possessing the immunological substance to be detected.

The reacted affixed surface is again impinged with substantially the same coherent radiation at substantially the same aspect and orientation previously utilized, and the pattern of radiation produced is again measured. Thereafter, the measured patterns of radiations are compared to determine any differentiations therebetween.

Figure 3:
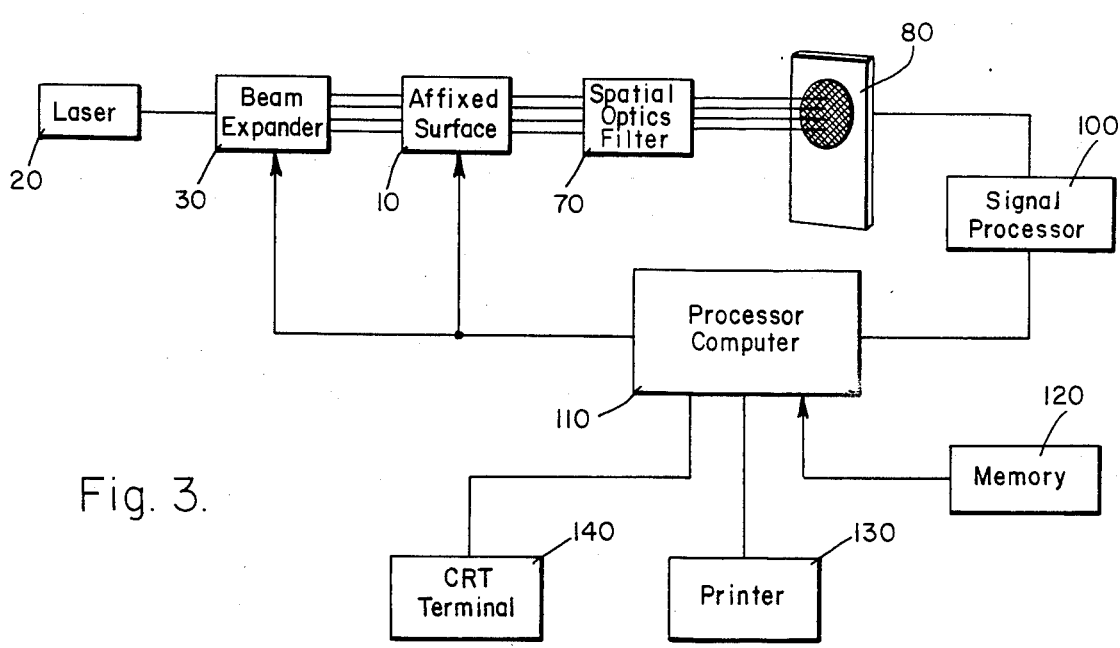
FIG. 3 schematically illustrates yet another embodiment of the present invention providing a complete system for qualitative and quantitative analysis of a substance to be detected.

FIG. 3 illustrates yet another embodiment of the present invention providing a complete system for qualitative and quantitative analysis of the immunological substance to be detected.

In the third embodied form, coherent radiation derived for example, from a laser source 20 produces a beam which is expanded by suitable means such as a beam expander 30 and impinged on the affixed surface 10.

Spatial filtering optics 70 provide a resultant signal which is detected, for instance, by photometric detector means 80. The photometric detector means 80 is preferably connected with a suitable signal amplifier means 90 which amplifies the derived photometric signal. Thereafter, the amplified signal is fed to a signal processor 100 for transmission in digital form and fed to a central processing unit 110, for instance a suitable microprocessor unit.

Preferably incorporated with the central processing unit 110 is a memory means 120, an output printer means 130, and a cathod ray tube (CRT) terminal 140 providing user and program control for the system. The affixed surface 10 may be reoriented appropriately for impingement and measurement by programmed means incorporated into the central processing unit 110. Spatial filtering optics 70 may also be programmed by the central processing unit 110.

Figure 4:
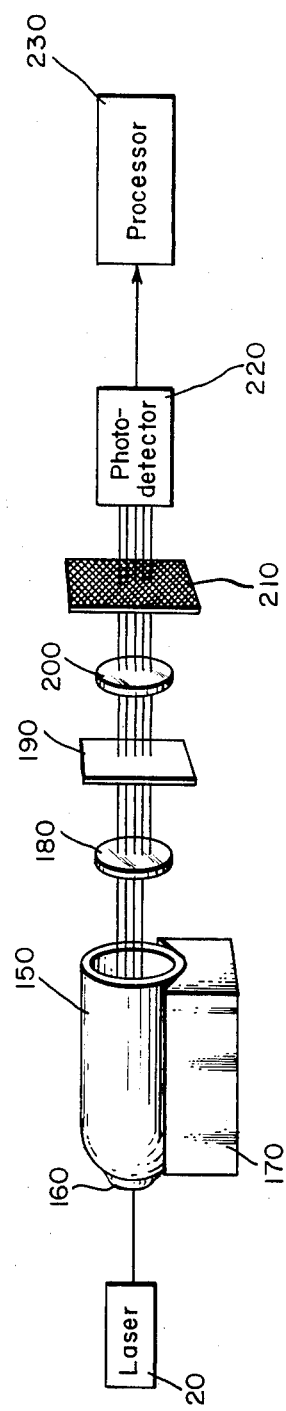
FIG. 4 schematically illustrates a presently preferred embodiment in accordance with the present invention wherein spatial filtering technique is utilized for detection of surface changes.

In a presently preferred embodiment, depicted in FIG. 4, the inventive method and instrumentation is utilized in conjunction with a cylindrical surface such as a transparent vial or test tube 150 composed of suitable material. Such materials are disclosed for instance in U.S. Pat. No. 3,720,760, issued on Mar. 13, 1973 to Bennich et al, which is hereby incorporated by this reference. The tube 150 comprises a diffuser 160 at the base portion thereof. For instance, a small diffuser or button which may be formed during molding of the vial.

Water insoluble polymers are used as a carrier for the test allergen in the Bennich method. Polymers, for example, in the form of flat objects such as discs or strips or also, for example, in the form of a wall of a tube such as the internal side of a test tube can be utilized. The bond between the polymer and the test allergen should be such that in normal washing procedures the test allergen cannot be released from the polymer. To this effect, it may, for instance, be of chemical or optionally physical nature. A suitable form of chemical binding is to provide bridges of covalent character between the polymer and the test allergen. For this purpose, the polymer is selected so that it contains or can be provided with suitable reactive groups, for instance, amino groups, hydroxyl groups, and carboxyl groups, to enable the test allergen to be bound easily to the polymer. For this purpose, bridges between the polymer and allergen with chemical bonds of a covalent character are preferably selected.

It is particularly suitable to select polymers consisting of a 3-dimensional network held together by bonds of a covalent character. Such polymers, even though they are swellable in water or aqueous media, are completely insoluble and thus cannot release any of the polymeric material or the substances bound thereto, for instance, during washing procedure.

The test allergen is bound to the carrier polymer under mold conditions, in order not to appreciably reduce the immunochemical reactivity of the allergen.

Used in chemically binding the allergen to the polymer are such reactive groups as amino groups, hydroxyl groups, mercapto groups, amido groups, and carboxyl groups, a bridge formed having chemical bonds, preferably of covalent character, from the test allergen to the polymer.

The polymer with substance attached thereto can be readily separated from fluid. The separation is insensitive to variations in salt and protein concentration of the fluid within physiological limits.

The quantity of polymers having allergen bound thereto is selected inter alia with thought to the level of sensitivity required during the test. The quantity of antibodies against reagin-Ig added to the reaction is selected, for instance, so that there is an excess in relation to the number of combining sites for these antibodies on the attached substances of the polymers after the allergens have been completely saturated with reagin-Ig.

Specific illustrative examples of Bennich as disclosed in U.S. Pat. No. 3,720,760, are applicable to the protocol of the instant invention. Those skilled in the art in RIA and ELISA assay, will readily appreciate the parameters and conditions for reaction in accordance with the present invention.

The diffuser 160 acts as a very short focal length lens to couple a substantial portion of incident laser light into the interior of the tube, much in the form of a wave guide.

The tube 150 is preferably held by holding means 170 to position and center the longitudinal axis of the tube 150 in the path of the laser beam axis. A variety of complex internal reflections permit the exposure of the affixed surface 150' to the coherent radiation, a portion of such radiation being transmitted through and out of the open portion of the tube 150. The escaping radiation from the tube 150 is directed toward a first lens means 180.

At the focal plane of lens means 180 an aperture means 190 is positioned to select the central portion of the beam (if high frequency is desired) or to block the central portion of the beam (if low frequency is desired).

A second lens means 200 is positioned at a distance from the screen 210 substantially equal to its focal length. Accoringly, an image is produced upon a photo detector means 220 transmitting the derived signal from the incident image to a processor unit means 230.

The foregoing embodiment permits spatial filtering of high or low frequency features of the speckle pattern, which is readily appreciated by those skilled in the art. Since the speckle pattern will generally correspond to higher frequency components, any regular structure appearing after the surface has reacted will be of lower frequency whose visibility may be augmented by the aforementioned or other known means, including, but not limited to, pattern recognition procedures, rotating grids and masks, as well as other type of signal processing and enhancement techniques.

The spatial filtering technique illustrated in FIG. 4 is merely illustrative procedure for the detection of surface changes associated with the formation of regular structures as has been heretofore described. For more subtle changes, it will be apparent that digital processing techniques are applicable and preferred.

In particular, if the pattern image is projected on a multipixel detection device such as a Reticon array of the type manufactured by EG & G, then each resolution cell of the image, corresponding to the size of the pixel, will yield a digital value for storage in a computer memory means characteristic of the photon flux incident upon the pixel during the time of measurement.

After exposing the affixed surface to react a material and re-examining under substantially similar conditions of radiation impingement, another set of pixel values may be generated and stored digitally. With the information stored concerning the two scattered patterns in a computer means, it is a relatively straightforward task to perform a correlation calculation between the two or more sets of digitilized pixel values. Small correlation corresponds to higher reactant concentrations and visa versa.

Analysis and comparison of such complex scatter patterns of radiation and interference of coherent radiation from a prepared surface may be enhanced by examining the various features of the pattern produced at different orientations to the incident source of radiation.

Figure 5:
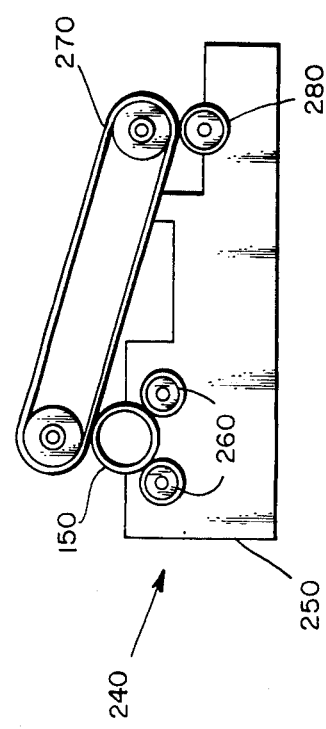
FIG. 5 illustrates unique means for periodic rotation of the affixed surface co-axially with the incident coherent radiation beam thereby producing a rotation of the scatter pattern.

In this latter respect, FIG. 5 illustrates means for examining the affixed surface and reacted affixed surface at different orientations to the incident source. Illustrated in one embodied form is means 240 providing periodic rotation of the surface (in this case a tube 150) and co-axially aligned with the incident laser beam and photodetector or digital detector array. The tube 150 is mounted on support means 250 with its peripheral surface resting on cylindrical bearings 260 permitting free rotation.

A friction belt 270, for instance composed of rubber or the like, is positioned contiguous against the outer surface of the tube 150 to provide an additional contact point.

Motor means 280 drives the belt 270 against the external surface of the tube 150 resulting in rotation of the tube 150 and corresponding rotation of the scatter pattern eminating from the open end of the tube 150.

With rotation of the tube 150 and corresponding rotation of the scatter pattern, the scatter pattern may be accordingly analyzed by the aforedescribed analysis methods and averaged over time and/or orientation. The precision of the final comparison of patterns of radiation to determine any differentiations therebetween may thus be conveniently enhanced in accordance with yet another feature of the present invention.

While the foregoing description has generally referred to specific immunological substances to be detected and quantified, as well as referring to radiation in the visible spectrum, those skilled in the art will readily appreciate that a multitude of particular chemical substances can be determined and the inventive system may use radiation in the non-visible spectrum, such as x-rays, ultraviolet and infra red radiation. Moreover, the medium or media containing the chemical substance to be detected may be a liquid such as water, a mixture of gases such as air, or may be a solid such as earth. Accordingly, a full range of detection possibilities having a very broad range of applicability for chemical substances of biological origin based on the use of coherent radiation is comprehended.

As applied to immunological substances to be detected and quantified, those skilled in the art will readily appreciate the full range of surfaces to be affixed and class of reactant materials useful in carrying out the present invention. The disclosure of U.S. Pat. No. 3,720,760, issued on Mar. 13, 1973 to Bennich et al, and assigned to Pharmacia, is hereby expressly incorporated by reference.

Accordingly, the present invention fulfills the significant need for a sensitive yet relatively rapid detection and quantitation technique which has application to a broad range of biological fields.

It will be apparent from the foregoing that, while particular forms of the invention have been illustrated and described, various modifications can be made without departing from the spirit and scope of the invention. Accordingly, it is not intended that the invention be limited except by the appended claims.

We claim:

1. A method for detecting the presence of an immunological substance in a medium, said method comprising the steps of:
    (a) preparing a water insoluble polymeric surface by affixing thereto a material which chemically reacts with and specifically binds with the immunological substance sought to be detected; said affixing being effected by groups selected from the group consisting of amino groups, hydroxyl groups, mercapto groups, amido groups, and carboxyl groups;
    (b) washing said prepared surface derived from step (a) to substantially remove unbound material;
    (c) drying said prepared surface derived from step (b);
    (d) impinging said prepared surface with a source of coherent or partially coherent radiation;
    (e) measuring a pattern of radiation scattered from said prepared surface;
    (f) reacting said prepared surface with a medium that may contain said immunological substance sought to be detected;
    (g) washing said prepared surface derived from step (f) to substantially remove excess medium;
    (h) drying said prepared surface derived from step (g);
    (i) impinging the reacted prepared surface derived from step (h) with substantially the same radiation at substantially the same aspect and orientation utilized to perform step (d);
    (j) measuring a pattern of radiation scattered from said reacted prepared surface;
    (k) recording said patterns of radiation derived from steps (e) and (j); and (l) comparing said patterns of radiation derived from steps (e) and (j) to determine any differentiations therebetween.

2. The method as defined in claim 1 and further comprising the step of incubating said affixed surface with said medium containing said immunological substance.

3. The method as defined in claim 1 and further comprising the step of quantitating any differentiations between said patterns of radiation derived from steps (b) and (f) as a measure of the presence and amount of said immunological substance to be detected.

4. The method as defined in claim 1 wherein said coherent radiation is produced by a laser.

5. The method as defined in claim 4 wherein said laser produces coherent radiation in the visible spectrum.

6. The method as defined in claim 4 wherein said laser produces radiation in the non-visible spectrum.

7. The method as defined in claim 4 wherein said laser produces x-ray radiation.

8. The method as defined in claim 4 wherein said laser produces coherent infra red radiation.

9. The method as defined in claim 4 wherein said laser produces coherent ultraviolet radiation.

10. The method as defined in claim 1 wherein said immunological substance is a native protein.

11. The method as defined in claim 1 wherein said immunological substance is a complex protein.

12. The method as defined in claim 1 wherein said immunological substance is an antibody.

13. The method as defined in claim 1 wherein said immunological substance is an antigen.

14. The method as defined in claim 1 wherein said immunological substance is an allergen.

15. The method as defined in claim 1 wherein said pattern of radiation scattered results from the changing of an incident radiation associated with its change of direction.

16. The method as defined in claim 1 wherein said pattern of radiation scattered results from the changing of an incident radiation associated with its change of frequency.

17. The method as defined in claim 1 wherein said pattern of radiation scattered results from the changing of an incident radiation associated with its change of intensity.

18. The method as defined in claim 1 wherein said pattern of radiation scattered results from the changing of an incident radiation associated with its change of polarization.

19. The method as defined in claim 1 wherein said surface is an interface separating two media.

20. The method as defined in claim 1 wherein said surface is an interface separating two phases.

21. The method as defined in claim 1 wherein said medium containing said immunological substance is human serum.

22. The method as defined in claim 1 wherein said medium containing said immunological substance is animal serum.

23. The method as defined in claim 1 wherein said recording is effected by impinging said patterns on an array of detectors and converting each detector signal into a representation of relative intensity detected thereon.

24. The method as defined in claim 23 wherein said recorded patterns are compared with each other by calculating mathematical correllation between corresponding array elements of each pattern.

25. The method as defined in claim 24 wherein the quantity of immunological substance to be detected is derived from the degree of correllation between said corresponding array elements of said patterns.

26. The method as defined in claim 1 wherein medium containing said immunological substance is water.

27. The method as defined in claim 1 wherein said medium containing said immunological substance is air.

28. The method as defined in claim 1 wherein said medium containing said immunological substance is gaseous.

29. The method as defined in claim 1 wherein said medium containing said immunological substance is liquid.

30. The method as defined in claim 1 wherein said medium containing said immunological substance is solid.

* * * * *